United States Patent [19]

Manning

[11] Patent Number: 4,678,501

[45] Date of Patent: Jul. 7, 1987

[54] CERTAIN PYRAZINYL 1,3 CYCLOALKANEDIONE DERIVATIVES HAVING HERBICIDAL ACTIVITY

[75] Inventor: David T. Manning, Charleston, W. Va.

[73] Assignee: Union Carbide Corporation, Danbury, Conn.

[21] Appl. No.: 817,177

[22] Filed: Jan. 9, 1986

Related U.S. Application Data

[63] Continuation of Ser. No. 288,335, Jul. 30, 1981, abandoned.

[51] Int. Cl.$^4$ .................. A01N 43/60; C07D 241/00
[52] U.S. Cl. ........................................ 71/92; 544/336; 544/335; 544/224; 546/340

[58] Field of Search ............................. 544/336; 71/92

[56] References Cited

U.S. PATENT DOCUMENTS

| 4,209,532 | 6/1980 | Wheeler | 514/683 |
| 4,436,666 | 3/1984 | Wheeler | 558/248 |

*Primary Examiner*—Alan L. Rotman
*Attorney, Agent, or Firm*—Morgan & Finnegan

[57] ABSTRACT

Novel aromatic heteromonocyclic-substituted 1,3-cycloalkanediones, enol ester derivatives and salts thereof, exhibit herbicidal activity against a variety of broadleaf and grassy weeds. Certain 2-(2-pyrazinyl) 1,3-cycloalkanediones and their enol esters were also found to be active as mite adulticides and ovicides.

10 Claims, No Drawings

CERTAIN PYRAZINYL 1,3 CYCLOALKANEDIONE DERIVATIVES HAVING HERBICIDAL ACTIVITY

This application is a continuation of prior U.S. application Ser. No. 288,335 filed July 30, 1981, now abandoned.

FIELD OF THE INVENTION

This invention relates in general to novel heteroaryl-substituted 1,3-cycloalkanediones and derivatives thereof. In one aspect, this invention relates to novel compositions which exhibit herbicidal activity against a variety of broadleaf and grassy weeds. In a further aspect, this invention relates to certain derivatives of the compositions which also are active as mite adulticides and ovicides.

DESCRIPTION OF THE PRIOR ART

Prior to the present invention certain heterocyclic alkanediones had been investigated for their antihypertensive properties. For example, T. Tsujikawa et al., in Heterocycles 6 (3) 261–266 (1977) reported certain tetrahydropyridinyl 1,3-cyclohexanediones and related hydrogenated 5-, 6- and 7-ring compounds. These and other related compounds were invariably described in the literature as having an exocyclic double bond joining the two ring systems:

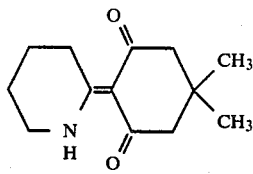

and hence are non-aromatic heterocyclic compounds.

Other compounds which have been reported in the literature are the isomeric 2-pyridinyl 1,3-indanediones or pyrophthalones, such as

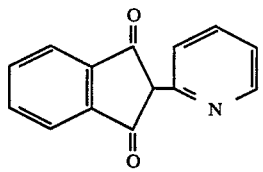

See for example, the works of J. Ploquin, et al., Eur. J. Med. Chem.—Chim. Ther. 9 (5), 519–525; 526–533 (1974), J. G. Lombardino, J. Org. Chem. 32, 1988–1982 (1967), J. Kacens, et al., C.A. 78, 57523 n (1973) and K. Buggle and M. Nangle, Chem. & Ind. (1976) 111–112.

Japanese Pat. No. 73/11,097 which issued Apr. 10, 1973 to Sankyo describes certain herbicidal thiazolidines including compounds such as:

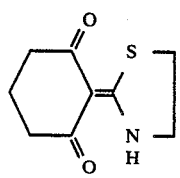

while K. Hirai, et al., Chem. Pharm. Bull. 20, 1711–1715 (1972), discloses compounds such as

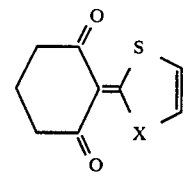

wherein X is S or O.

Pyridinium betaines such as

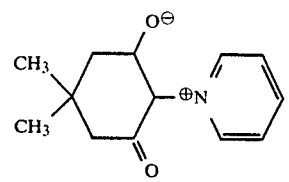

have been disclosed by B. Karele, and O. Neilands, Chem. Abs. 85 20763; (1976).

References are also made in the literature to bicyclic 1,3-cycloalkanediones, such as

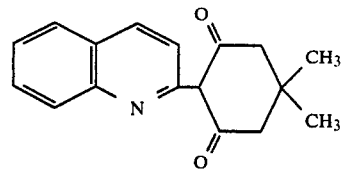

reported by J. E. Douglass and H. D. Fortner, J. Het. Chem. 10, 115–116 (1973).

Few of the aforementioned literature references discloses aromatic, heteromonocyclic-sybstituted 1,3-cycloalkanediones, much less make any mention of herbicidal or miticidal activity. Moreover, six-membered monocyclic aromatic nitrogen heterocycles joined by a carbon atom to the dione ring at the 2-position were not known prior to this invention.

DESCRIPTION OF THE INVENTION

In its broad aspect, this invention is directed to novel compositions, processes for their preparation, herbicidal and miticidal compositions and uses thereof. The novel compositions of this invention can be conveniently represented by the following formula:

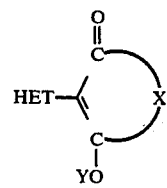

wherein X is a 2 or 3 member alkylene chain which may be substituted with one or more alkyl or alkenyl, wherein the permissible substituents are one or more alkyl, cyano, halogen, nitro, alkoxy, alkylthio, alkylsulfinyl, alkylsulfonyl, dialkylamino, acylamido or acyl substituents, or any two substituents together may form an alkylene or alkenylene chain having from 2 to 6 carbon atoms completing a 3,4,5,6 or 7-membered ring structure, with the proviso that when X is a 2-membered alkylene chain substituents thereon when taken with X do not form an aromatic ring;

Y is hydrogen, any salt forming cation (Na⊕, NH₄⊕, Ca ⊕⊕ , etc), and

where Z is hydrogen, halogen, alkyl, alkoxy, alkylthio, amino, alkylamino, dialkylamino, alkenyl, alkynyl, bicycloalkyl, bicycloalkenyl, cycloalkyl, cycloalkenyl, phenyl, phenylalkyl, naphthyl or naphthylalkyl all of which except hydrogen and halogen may be substituted with one or more alkyl, carboxy, cyano, nitro, alkoxy, alkoxycarbonyl, halogen, haloalkyl, alkoxyalkyl, alkylthio, alkylsulfinyl, alkylsulfonyl, alkylsulfinylalkyl, alkylsulfonylalkyl, alkylthioalkyl or dialkylamino substituent, or Z is

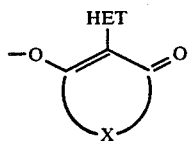

wherein X is as above and;
HET is selected from the group of:

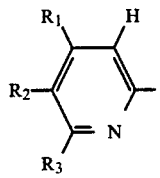 (I)

wherein
$R_1$ is H, alkyl ($C_1$-$C_5$), alkoxy ($C_1$-$C_4$), alkylthio ($C_1$-$C_4$), alkylsulfinyl ($C_1$-$C_4$), alkylsulfonyl ($C_1$-$C_4$), alkenyl ($C_2$-$C_5$), alkylamino ($C_1$-$C_4$), dialkylamino ($C_2$-$C_5$), amino, hydroxy, alkoxyalkyl ($C_2$-$C_4$), alkylthioalkyl ($C_2$-$C_4$), alkylsulfinylalkyl ($C_2$-$C_4$), alkylsulfonylalkyl ($C_2$-$C_4$), trifluoromethoxy, halogen, haloalkyl or polyhaloalkyl, with the longest straight chain of atoms being 3 or less in number;
$R_2$ is H or alkyl ($C_1$-$C_2$);
$R_3$ is H, $CH_3$, alkoxy ($C_1$-$C_2$), or alkylthio ($C_1$-$C_2$), with the longest straight chain of atoms being 3 or less in number;

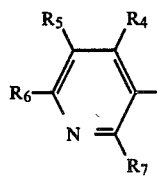 (II)

wherein
$R_4$, $R_5$ and $R_6$, individually, are H, haloalkyl, halogen, alkyl ($C_1$-$C_5$), polyhaloalkyl, alkoxy ($C_1$-$C_4$), alkylthio ($C_1$-$C_4$), hydroxy, amido, amino, alkylsulfonyl ($C_1$-$C_4$), alkylamino, dialkylamino, or alkylsulfinyl ($C_1$-$C_4$).

$R_7$=alkyl ($C_1$-$C_3$), halogen, haloalkyl or polyhaloalkyl;

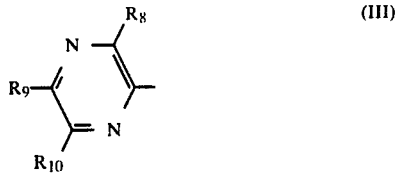 (III)

wherein
$R_8$ is H, alkyl ($C_1$-$C_4$), halogen, alkoxyl ($C_1$-$C_3$), alkylthio ($C_1$-$C_3$), haloalkyl, polyhaloalkyl, alkoxyalkyl ($C_2$-$C_4$), alkylthioalkyl ($C_2$-$C_4$), alkylsulfinylalkyl ($C_2$-$C_4$) or alkylsulfonylalkyl ($C_2$-$C_4$);
$R_9$ is H, alkyl ($C_1$-$C_4$), alkenyl ($C_2$-$C_4$), haloalkyl, halogen, polyhaloalkyl, alkoxy ($C_1$-$C_3$), or alkylthio ($C_1$-$C_3$), with the longest straight chain of atoms being 4 or less in number;
$R_{10}$ is H, methyl, ethyl, alkoxy ($C_1$-$C_3$) or alkylthio ($C_1$-$C_3$);

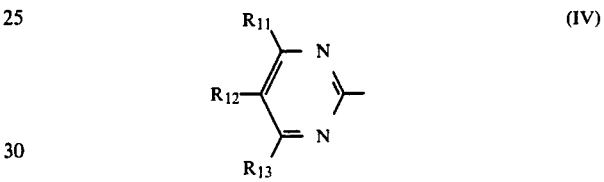 (IV)

wherein $R_{11}$ and $R_{13}$ are the same as $R_1$ and $R_{12}$ is the same as $R_9$ with the proviso that the total number of carbon atoms for $R_{11}$, $R_{12}$ and $R_{13}$ is no greater than 8;

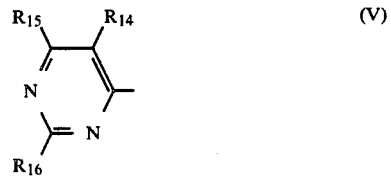 (V)

wherein $R_{14}$ is the same as $R_8$; $R_{15}$ is the same as $R_1$ and $R_{16}$ is the same as $R_9$, with the proviso that the total number of carbon atoms for $R_{14}$, $R_{15}$ and $R_{16}$ is no greater than 8;

(VI)

wherein $R_{20}$ is the same as $R_8$; $R_{21}$ is the same as $R_1$, and $R_{22}$ is hydrogen or methyl.

(VII)

wherein $R_{23}$ and $R_{24}$ are the same as $R_8$, and $R_{25}$ is the same as $R_1$, with the proviso that the total number of carbon atoms for $R_{23}$, $R_{24}$ and $R_{25}$ is no greater than 8; and at least one of $R_{23}$, $R_{24}$ and $R_{25}$ is other than hydrogen.

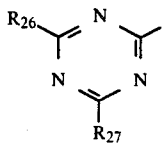
(VIII)

wherein $R_{26}$ and $R_{27}$ are H, alkyl ($C_1$–$C_5$), alkoxy ($C_1$–$C_4$), alkylthio ($C_1$–$C_4$), alkenyl ($C_2$–$C_5$), alkylamino ($C_1$–$C_4$), dialkylamino ($C_2$–$C_5$), amino, hydroxy, alkoxyalkyl ($C_2$–$C_4$), alkylthioalkyl ($C_2$–$C_4$), alkylsulfinylalkyl ($C_2$–$C_4$), alkylsulfonylalkyl ($C_2$–$C_{14}$), trifluoromethoxy or haloalkyl with the longest straight chain of atoms being 3 or less in number and a maximum of 5 carbon atoms for all carbon-containing substituents.

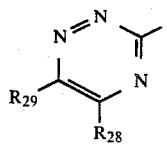
(IX)

wherein $R_{29}$ and $R_{28}$ are the same as $R_{26}$ and $R_{27}$;

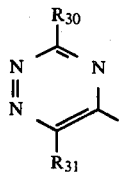
(X)

wherein $R_{30}$ is the same as $R_{26}$ and $R_{31}$ is the same as $R_8$; and

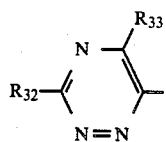
(XI)

wherein $R_{32}$ is the same as $R_9$ and $R_{33}$ is the same as $R_8$;

It should be noted that when Y in the generic formula above is hydrogen, the ring to which Y O is attached can exist in its tautomeric 1,3-cyclodione form:

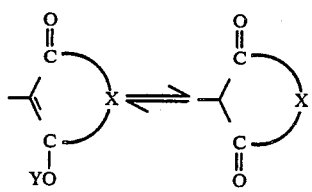

wherein X is as indicated above.

Illustrative compositions which can be prepared in accordance with the teachings of this invention include, among others:

5-(1-Methylethyl)-2-(4-methylthio-2-pyridinyl)-1,3-cyclohexanedione,
2-(4-Dimethylamino-2-pyridinyl)-5-(1-methylethyl)-1,3-cyclohexanedione,
2-(4-Methoxy-6-methyl-2-pyridinyl)-5-(1-methylethyl)-1,3-cyclohexanedione,
5-Ethyl-2-(4-methoxy-2-pyridinyl)-5-methyl-3-pentanoyloxy-2-cyclohexen-1-one,
5-Methyl-5-(1-methylethyl)-2-(4-methyl-2-pyridinyl)-1,3-cyclohexanedione;
3-Butanoyloxy-5-methyl-5-(1-methylethyl)-2-(4-methyl-2-pyridinyl)-2-cyclohexen-1-one,
2-(4-Methoxy-2-pyridinyl)-5-methyl-5-(1-methylethyl)-1,3-cyclohexanedione,
2-(4-Methoxy-2-pyridinyl)-5-(2-propenyl)-1,3-cyclohexanedione,
5-Methyl-2-(4-methyl-2-pyridinyl)-1,3-cyclohexanedione,
5-(1-Methylpropyl)-2-(3-pyridinyl)-1,3-cyclohexanedione,
5-Ethyl-3-hexanoyloxy-5-methyl-2-(4-methyl-3-pyridinyl)-2-cyclohexen-1-one,
4-Methyl-2-(2-pyridinyl)-1,3-cyclopentanedione,
2-(4-Ethoxy-2-pyridinyl)-4,4,5,5-tetramethyl-1,3-cyclopentanedione,
2-(3-Ethyl-2-pyrazinyl)-5-(1-methylethyl)-1,3-cyclohexanedione,
5-Methyl-5-(1-methylethyl)-3-pentanoyloxy-2-(2-pyrazinyl)-2-cyclohexene-1-one
2-(5-Methoxy-3-methyl-2-pyrazinyl)-5-methyl-5-(1-methylethyl)-1,3-cyclohexanedione,
2-(5,6-Dimethyl-4-pyrimidinyl)-5-(1-methylethyl)-1,3-cyclohexanedione,
2-(6-Methoxy-5-methyl-4-pyrimidinyl)-5-methyl-5-methoxymethyl-3-propanoyloxy-2-cyclohexen-1-one,
2-(4,6-Dimethyl-5-pyrimidinyl)-1,3-cyclopentanedione;
2-(4,5-Dimethyl-3-pyridazinyl)-5-(2-ethylthiopropyl)-1,3-cyclohexanedione;
5,5-Dimethyl-2-(3,5-dimethyl-4-pyridazinyl)-3-octanoyloxy-2-cyclohexen-1-one,
5,5-Diethyl-2-(2-pyrimidinyl)-1,3-cyclohexanedione,
8-[2-(1,3,5-triazinyl)]-spiro[4.5]decane-7,9-dione,
2-[5-Ethyl-3-(1,2,4-triazinyl)]-5-(1-methylethyl)-1,3-cyclohexanedione,
2-[6-Methyl-5-(1,2,4-triazinyl)]-5-(1-methylethyl)-1,3-cyclohexanedione, and
2-[5-Ethyl-6-(1,2,4-triazinyl)]-3-hexanoyloxy-5-(trifluoromethyl)-2-cyclohexen-1-one.

Preferred compositions which are encompassed by the generic formula, include:

5,5-Dimethyl-2-(2-pyridinyl)-1,3-cyclohexanedione,
5,5-Dimethyl-2-(2-Pyridinyl)-1,3-cyclohexanedione sodium salt,
5,5-Dimethyl-2-(4-methyl-2-pyridinyl)-1,3-cyclohexanedione,
5-(1-Methylethyl)-2-(2-pyridinyl)-1,3-cyclohexanedione,
5-(1-Methylethyl)-2-(4-methyl-2-pyridinyl)-1,3-cyclohexanedione,
2-(4-Ethyl-2-pyridinyl)-5-(1-methylethyl)-1,3-cyclohexanedione,
2-(4-Methoxy-2-pyridinyl)-5-(1-methylethyl)-1,3-cyclohexanedione,
8-(2-pyridinyl)-spiro[4.5]decane-7,9-dione,
5-Ethyl-5-methyl-2-(2-pyridinyl)-1,3-cyclohexanedione, 5-(1-Methylpropyl)-2-(2-pyridinyl)-1,3-cyclohexanedione, 5-(1,1-Dimethylethyl)-2-(2-pyridinyl)-1,3-cyclohexanedione, 5-(1-Ethylpropyl)-2-(2-pyridinyl)-1,3-cyclohexanedione, 5,5-Dimethyl-2-(3,5,6-trimethyl-2-pyrazinyl)-1,3-cyclohexanedione, 5,5-Dimethyl-3-hexanoyloxy-2-(3,5,6-trimethyl-2-pyrazinyl)-2-cyclohexene-1-one, 5-(1-Methylethyl)-2-(3,5,6-trimethyl-2-pyrazinyl)-1,3-cyclohexanedione, 3-Hexanoyloxy-5-(1-methylethyl)-2-(3,5,6-trimethyl-2-pyrazinyl)-2-cyclohexen-1-one, 5,5-Dimethyl-3-(2-methylpropanoyloxy)-2-(3-methyl-2-pyrazinyl)-2-cyclohexene-1-one, and 8-(3,5,6-Trimethyl-2-pyrazinyl)-spiro[4.5]decane-7,9-dione In practice, the novel dione compositions of this invention can be prepared by the reactions of heterocyclic lithium derivatives in accordance with the procedure of Edwards and Teague, JACS 71, 3548 (1949):

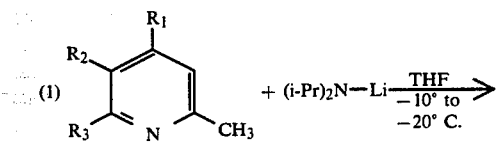

(1)

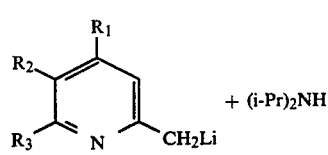

(2)

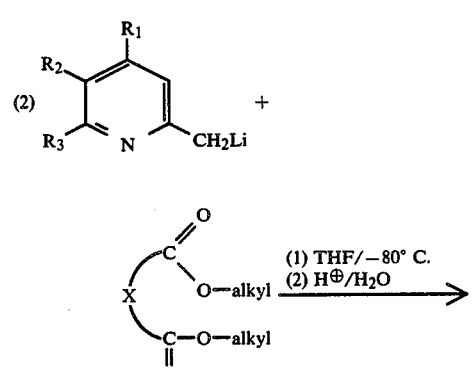

dicarboxylic ester
reactant

-continued

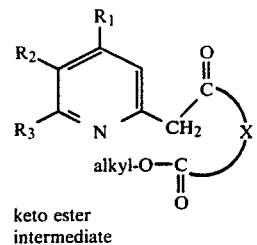

keto ester
intermediate

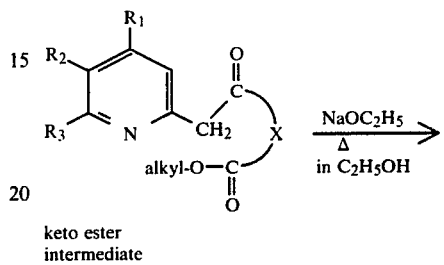

keto ester
intermediate

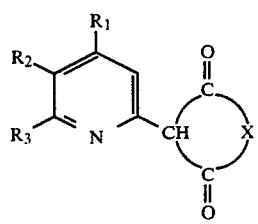

substituted 2-(2-pyridinyl)-
1,3-cycloalkanidione

The lithium diisopropylamide (LDA) of step (1) is prepared by reaction of n-butyllithium (or other alkyllithium) with diisopropylamine and the 2-methylpyridine is then added to the mixture giving the 2-pyridylmethyllithium. The resulting solution in tetrahydrofuran (THF) is then fed, with care to exclude air and moisture, to a 200 percent excess of the dicarboxylic ester (such as diethyl 3,3-dimethylglutarate) at about −80° C. (Use of excess ester minimizes double addition of the organolithium reagent). The keto ester is worked up by neutralization of its basic solution and finally purified by vacuum distillation in a short-path apparatus. In the final step (3), cyclization of the keto ester to dione is conducted by refluxing with 1 mol of sodium ethoxide in ethanol. In addition to 2-methylpyridines, methyl and methylene groups at the pyridine 4-position are also highly activated and react rapidly with organolithium reagents to form lithium salts analogous to the above. Such lithium derivatives of 4-methyl groups, or the ethyl methylene groups in either the 2- or 4-position, however, do not lead to the desired compounds. If a 2-methylpyridine bears an additional methyl or ethyl group at position 4, (i.e., R is —CH₃ or —CH₂CH₃) one must employ an alkyllithium (C₄H₉Li, etc.) or phenyllithium reagent

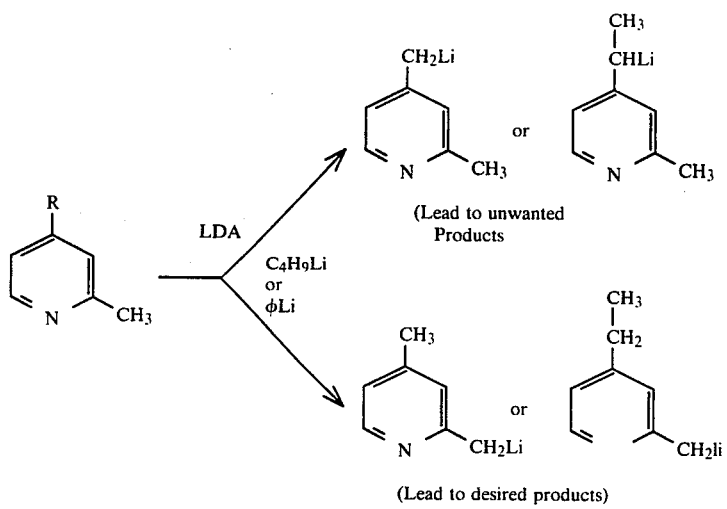

(Lead to unwanted Products)

(Lead to desired products)

in place of LDA to achieve lithiation at 2-methyl rather than upon the 4-alkyl substituent. The alternate use of alkyl- and phenyllithium reagents to achieve this selective lithiation has been described by Kaiser, et al, J. Org. Chem. 38,71 (1973) and by Arens et al., Rec. Trav. Chim. 69, 287 (1950).

When pyridines bear methyl groups at positions both alpha and beta to the ring nitrogen then organolithium (and other organometallic) reactions occur preferentially at the activated alpha-attached group as indicated.

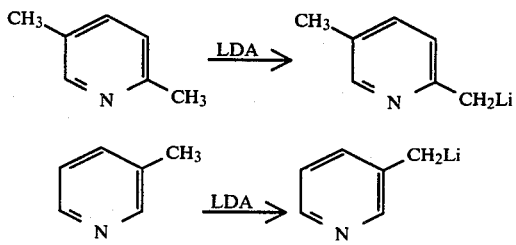

When no activated methyl group is present, as with 3-picoline the metallation procedure still occurs but it is less facile and the intermediate formed is a much more reactive species.

The enol esters of the diones are conveniently prepared by treatment of the dry potassium salts of the diones with an equivalent of acid chloride and a small amount of dicyclohexyl-18-crown-6, as a stirred slurry in dry THF. Following the reaction the stripped residue is extracted with ether and the latter solution washed quickly with 0.2N NaOH at 0°-5° C. to remove unreacted dione. (Filtration through silica gel or extraction with 7% aqueous TEA will remove any unreacted acid chloride indicated by the IR spectrum). The ether solutions are then dried over $MgSO_4$, filtered and stripped to give the desired esters.

In general, the process conditions and reaction variable used in the synthesis of the compositions of this invention, will depend, in part, upon the particular reagents employed. For example, in the keto ester formation from 2,4-dimethylpyridines, alkyllithiums and phenyllithiums are the reagents employed. For all other methyl heterocycles in addition to LDA, alkyl-, and phenyllithiums, sodium amide, potassium amide and combinations of these amides with sodium and potassium tert-butoxide may be feasible for the deprotonation step.

The overall mole ratio of methyl heterocycle to organometallic reagent to dicarboxylic ester is from about 1:0.1:1 to from 1:2.10 and more preferably about 1:1:3.

Although a variety of solvents can be employed in the keto ester formation step, such as ethyl ether, isopropyl ether, dioxane, ethylene glycol dimethyl ether and benzene, tetrahydrofuran is preferred.

Temperatures for the reaction of heterocycle and organometallic base can range from about −80° C. to about +10° C. and preferably from about −10° C. to about −20° C. Reaction temperatures for the dicarboxylic ester condensation are from about −100° C. to about −50° C. and preferably about −80° C. The subsequent holding temperature is from about −10° C. to about +10° C. and preferably about 0° C. for a period of from about 0.5 to about 36 hours and preferably from about 4 to 16 hours.

The preferred neutralization agent is carbon dioxide, although hydrochloric, sulfuric or phosphoric acids can be employed as well as ammonium chloride.

For cyclization of the keto ester to the dione sodium ethoxide is the preferred base although other alkali alkoxides such as potassium ethoxide may be used. The reaction is conducted in a mole ratio of base to keto ester of from about 0.1:1 to about 5:1 and preferably 1:1 and at a temperature of from about room temperature to about 150° C., preferably about 80° C. The reaction time can vary from about 1 minute to about 24 hours and preferably is from about 1.5 hours to about 3 hours. The choice of reaction solvent is not necessarily critical and any solvent not decomposed by the cyclization base can be employed. For example, ethylene glycol and its mono and diethers can be used with ethanol, propanol or isopropyl alcohol being preferred. For extraction ethyl ether or dichloromethane are the preferred solvent, although any solvent with limited water miscibility can be utilized. In many cases, however, the product crystallizes out and needs no extraction. Extraction is usually carried out at a pH of from about 3.5 to about 10 and more preferably between 5 and 8. It should be noted that the basic diones may also be recovered as mineral acid salts.

For the preparation of the enol esters, the parent dione, preferably the sodium or potassium salt thereof, is reacted with an acid anhydride or more preferably an acid chloride in a mole ratio of dione to acylating agent of from about 1:2 to about 2:1 and preferably 1:1. The reaction is conducted within the temperature range of from about 0° C. to about 50° C., more preferably from about 25° to about 35° C. and in a solvent such as tetrahydrofuran. Other solvents, such as dioxane, ethylene glycol dimethyl ether and the like can also be employed.

In the examples, certain of the starting materials were prepared in accordance with methods disclosed in the literature. For example, 2,3-dimethylpyrazine was prepared from 2,3-dimethyl-5,6-dihydropyrazine by the method of G. P. Rizzi, J. Org. Chem. 33, 1333 (1968) which itself was prepared by the procedure of T. Ishiguro and M. Matsumura, Yak. Zass. 78, 229 (1958). 4-Ethyl-2-methylpyridine was prepared by the procedure of Kaiser et al., J. Org. Chem. 38, 71 (1973). 4-Methoxy-2-picoline-N-oxide was prepared by reacting 4-nitro-2-picoline-N-oxide with methanolic potassium carbonate solution according to the general procedure of E. Profft et al., Germany (East) 69, 126; 10/5/69; Chem. Abs. 72, 90309w (1970). The crude product was not purified but was reacted directly with phosphorous trichloride in chloroform solution to give the known 4-methoxy-2-picoline starting material, based upon the general method of Herz and Tsai, J. Am. Chem. Soc. 76, 4184 (1954).

As indicated in the following examples, the aromatic heteromonocyclic-substituted 1,3-cycloalkanediones of this invention show significant toxicity to a variety of broadleaf and grassy weeds, under conditions of preemergent and/or postemergent application, and have potential utility as selective and non-selective herbicides. Moreover, certain of the substituted 2-(2-pyrazinyl)1,3-cycloalkanediones and their enol esters display toxicity to both adult mites and mite eggs as hereinafter indicated in the examples.

The following examples illustrate the best mode presently contemplated for the practice of this invention:

EXAMPLE 1

ETHYL 3,3-DIMETHYL-5-KETO-6-(2-PYRIDINYL)HEXANOATE

All glassware was dried overnight at 130° C. and assembled under dry nitrogen. All liquid transfers were conducted through a stainless steel cannula with nitrogen pressure.

A solution of n-butyllithium (0.6 mol) in hexane was fed to a stirred solution of dry diisopropylamine (60.7 g., 0.6 mol) in 600 ml of dry THF with cooling to −10° to −20°. 2-Picoline (55.9 g, 0.6 mol), dried over 3A molecular sieves, was then added, with stirring, to the original mixture over an 11-min. period holding the temperature at −10° to −20°. A 167 ml portion (0.1 mol) of the resulting solution of 2-picolyllithium in THF was then added to a solution of diethyl 3,3-dimethylglutarate (64.9 g, 0.3 mol) over a 2 hour period with stirring and cooling to −78°. The resulting mixture was allowed to warm to 0° and then held at this temperature for approximately 16 hours. Water (50 ml) was then added, with stirring, to the mixture, cooled to 0°–5°, and gaseous $CO_2$ then fed into the stirred mixture for approximately 85 minutes until the pH of the solution was 7–7.5. THF was then evaporated from the neutralized mixture under reduced pressure and the residue diluted with ether, filtering the ether solution to remove insoluble materials. The ether filtrate was extracted 4 times with 6N HCl and the combined acid extracts washed with one portion of ether. The pH of the aqueous layer was adjusted to 11 with aqueous 6N NaOH causing an oil to precipitate. This was extracted with ether and the ether extract washed with brine, dried ($MgSO_4$) and evaporated to give 12.55 g of crude oily keto ester. Flash distillation through a Kugelrohr apparatus gave 7.9 g of ester (30.0% yield), bp 130°–148°/0.1 mm; ir (KBr) 1725 cm$^{-1}$ (ester C=O). A 2.65 g fraction, bp 120°–125°/0.05 mm, from a redistillation gave the following nmr spectrum ($CDCl_3$) δ 1.0–1.5 (m, 9, ethyl $CH_3$ and $CH_3$—C—$CH_3$), 2.3–2.9 (m, 4, $CH_2$—C—$CH_2$), 3.8–4.4 (q plus s, 4, ethyl $CH_2$ plus pyridyl $CH_2$), 6.7–8.7 (m, 4, pyridine ring).

EXAMPLE 2

5,5-DIMETHYL-2-(2-PYRIDINYL)-1,3-CYCLOHEXANEDIONE

To a refluxing solution of 0.34 g (0.0147 mol) of sodium in 50 ml dry ethanol (distilled from Mg) was added 3.87 g (0.0147 g) of ethyl 3,3-dimethyl-5-keto-6-(2-pyridinyl) hexanoate over a 4 minute period. The mixture was then refluxed for 1.5 hour after which it was evaporated to dryness and the residue dissolved in water and extracted twice with ether, discarding the latter extracts. The pH of the aqueous layer was adjusted to 10 with HCl causing the product to separate as a white solid. It was recovered by extracting 3 times with $CH_2Cl_2$, readjusting the pH of the aqueous layer from 11 to 10 and again extracting 3 times with $CH_2Cl_2$. The combined, dried ($MgSO_4$) $CH_2Cl_2$ extracts were filtered and evaporated to give 2.48 g (77.6%) of a white solid, mp 161.5°–165°. Recrystallization from ethyl acetate gave 2.04 g (63.9% yield) of white fibrous crystals, mp 163°–165°; ir (KBr) 2500–3000 cm$^{-1}$ (H-bonded N or O), 1638 cm$^{-1}$ (conj C=O), 1553 cm$^{-1}$; nmr ($CDCl_3$) δ 1.1 (s, 6, $CH_3$), 2.45 (s, 4, $CH_2$), 7.0–8.2 (m, 3, pyridinyl protons at C-4,5 and 6), 9.3–9.6 (m, 1, pyridinyl C-3 proton).

Analysis Calcd. for $C_{13}H_{15}NO_2$: C, 71.86; H, 6.96, N, 6.45. Found: C, 71.71; H, 7.00; N, 6.64.

EXAMPLE 3

5,5-DIMETHYL-3-OCTANOYLOXY-2-(2-PYRAZINYL)CYCLOHEXEN-1-ONE

Octanoyl chloride (6.41 g, 0.039 mol) was fed at room temperature and over a 5 minute interval, to a stirred slurry of 5,5-dimethyl-2-(2-pyrazinyl)-1,3-cyclohexanedione potassium salt (10.0 g, 0.039 mol) and 1 drop of dicyclohexyl-18-crown-6 in 150 ml of THF (dried over 3A molecular sieves). The temperature increased from 24.5° to 31.5° and partial solution of solids was apparent after 12 minutes following completion of the feed. Stirring was continued for approximately 23 hours at which time the mixture was evaporated to dryness under vacuum. The residue was stirred with ether, the ether slurry filtered and the filtrate washed quickly, and in succession, with ice cold 0.25N NaOH (twice), 7% aqueous triethylamine and saturated aqueous NaCl. The ether layer was dried ($MgSO_4$), filtered and vacuum stripped to dryness giving 11.2 g (83.2%) of orange oily product; ir (KBr) 1755 cm$^{-1}$ (ester C=O), 1640–1665 (conj C=O, C=C), 1135 cm$^{-1}$, 1090 cm$^{-1}$; nmr ($CDCl_3$) δ 0.7–1.4 (m, 19, 3×$CH_3$ plus 5×$CH_2$), 2.1–2.7 (m, 6, $CH_2$ adj to C=O), 8.45–8.7 (m, 3, aromatic).

Analysis Calcd. for $C_{20}H_{28}N_2O_3$: C, 69.74; H, 8.19; N, 8.13. Found: C, 69.71; H, 8.33; N, 7.64.

EXAMPLE 4

5-(1-METHYLETHYL)-2-(2-PYRIDINYL)-1,3-CYCLOHEXANEDIONE

The subject compound was prepared from ethyl 3-(1-methylethyl)-6-(2-pyridinyl)-5-oxohexanoate and a sodium ethoxide solution according to the general procedure of Example 2, but employing a 2.83 hour reflux period following completion of the feed. On working up the reaction the ether-extracted aqueous phase was adjusted to pH 6 causing the product to separate as a tan solid which was extracted with ether, recovered by evaporation and recrystallized twice from cyclohexene to give a solid, mp 110°-112° C. The confirmatory elemental analysis is shown in Table II.

EXAMPLE 5

5-(1-METHYLETHYL)-2-(4-METHYL-2-PYRIDINYL)-1,3-CYCLOHEXANEDIONE

The procedure of Example 2 was used to prepare the title compound from ethyl 3-(1-methylethyl)-6-(4-methyl-2-pyridinyl)-5-oxohexanoate and sodium ethoxide using a 2 hour reflux period in ethanol. The product was liberated as an oil from the aqueous phase by adjusting the pH to about 5 and recovered by ether extraction. The ether extract was worked up giving a semi-solid which was recrystallized successively from ethyl acetate and isopropyl ether giving the product as a solid, mp 104.5°-106.5° C. The confirmatory elemental analysis is shown in Table II.

EXAMPLE 6

2-(4-METHOXY-2-PYRIDINYL)-5-(1-METHYLETHYL)-1,3-CYCLOHEXANEDIONE

The title compound was prepared from ethyl 6-(4-methoxy-2-pyridinyl)-3-(1-methylethyl)-5-oxohexanoate and ethanolic sodium ethoxide, refluxing for 2 hours according to the procedure of Example 2. The product separated from the aqueous phase as a yellow solid upon adjusting the pH to about 6 and was recovered by extraction with dichloromethane. Evaporation of the dried extract and recrystallization from acetonitrile gave the product as a white solid, mp 152°-154.5° C. The confirmatory elemental analysis is shown in Table II.

EXAMPLE 7

ETHYL 3,3-DIMETHYL-6-(4-METHYL-2-PYRIDINYL)-5-OXOHEXANOATE

A 1.9 molar solution of phenyllithium in benzeneethyl ether (95 ml, 0.18 mol) was added, with stirring, to 180 ml of dry tetrahydrofuran (THF) in a dry, argon-blanketed system (Example 1) cooled to −10° to −20° C. Continuing the stirring and cooling to −15° C., a 27.7 ml portion (0.18 mol) of dry 2,4-lutidine was added over a 7 minute period and the black solution stirred at −15° to −20° C. for 30 minutes. This solution was then fed, with stirring, to a solution of diethyl 3,3-dimethylglutarate (116.8 g, 0.54 mol) in 230 ml of dry THF, with cooling to −78° C. The resulting mixture was allowed to warm to 0° C. and then held at this temperature for approximately 16 hours. Water (60 ml) was then added, with stirring, to the mixture, at 0°-5° C., and gaseous $CO_2$ then fed in until the pH reached about 6 to 8 and a white solid had precipitated. The mixture was then worked up according to the general procedure of Example 1, flash distilling the crude product to give the yellow, oily ester over the approximate range of 120°-210° C./0.2 mm (Kugelrohr air temperature); ir (KBr) 1730 cm$^{-1}$ (ester C=O).

EXAMPLE 8

5-(1-METHYLETHYL)-2-(3,5,6-TRIMETHYL-2-PYRAZINYL)-1,3-CYCLOHEXANEDIONE POTASSIUM SALT 5-(1-Methylethyl)-2-(3,5,6-trimethyl-2-pyrazinyl)-1,3-cyclohexanedione (18.13 g, 0.062 mol) was dissolved in a solution of 4.1 g (0.062 mol) potassium hydroxide in 100 ml of water. The solution was filtered and the yellow filtrate stripped to dryness on a rotary evaporator and finally dried to constant weight in a vacuum oven. The weight of potassium salt was 20.28 g (99.0% of theory).

EXAMPLE 9

3-HEXANOYLOXY-5-(1-METHYLETHYL)-2-(3,5,6-TRIMETHYL-2-PYRAZINYL)-2-CYCLOHEXENE-1-ONE

The subject compound was prepared by reaction of 5-(1-methylethyl)-2-(3,5,6-trimethyl-2-pyrazinyl)-1,3-cyclohexanedione potassium salt (Example 8) with hexanoyl chloride employing the general procedure described in Example 3, but allowing the reaction mixture to stir at room temperature over the weekend. Following the reaction, the ether solution of crude product was extracted quickly with ice-cold 0.25N NaOH, dried (MgSO$_4$), filtered and evaporated to give a residue product showing some acid chloride contamination by IR examination. Dry-column chromatography using 1:1 ethyl acetate/hexane gave analytically pure material as shown by the elemental analysis of Table II.

In a manner similar to that employed in the above examples other 1,3-diones and derivatives were prepared from the appropriate keto ester precursors. Tables I, II, III and IV below, set forth the structures and identification of the precursors and dione derivatives, and Table V below indicates physical properties and elemental analysis of the 1,3-diones.

TABLE I

KETO ESTER PRECURSOR

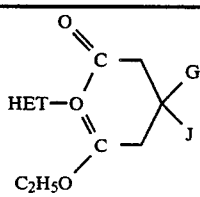

TABLE I-continued

KETO ESTER PRECURSOR

| COMPOUND | HET | G | J | ESTER C=O $\nu$ (Cm$^{-1}$) OR OTHER DATA |
|---|---|---|---|---|
| 1 | 2-Pyridinyl | CH$_3$ | CH$_3$ | 1725 |
| 2 | (sodium salt of Cmpd. 1) | CH$_3$ | CH$_3$ | 1725 |
| 3 | 4-Me—2-Pyridinyl | CH$_3$ | CH$_3$ | 1730 |
| 4 | 2-Pyridinyl | Me$_2$CH— | H | 1710 |
| 5 | 4-Me—2-Pyridinyl | Me$_2$CH— | H | 1730 |
| 6 | 4-Et—2-Pyridinyl | Me$_2$CH— | H | 1730 |
| 7 | 4-MeO—2-Pyridinyl | Me$_2$CH— | H | 1725 |
| 8 | 2-Pyridinyl | —(CH$_2$)$_4$— | | K.D.A.T.[a] 165°–190° C./0.4–0.5 mm. |
| 9 | 2-Pyridinyl | CH$_3$ | C$_2$H$_5$ | 1730 |
| 10 | 2-Pyridinyl | Me\\CH—/Et | H | 1730 |
| 11 | 2-Pyridinyl | Me$_3$C— | H | 1730 |
| 12 | 2-Pyridinyl | Et$_2$CH— | H | 1725 |
| 13 | 3,5,6-Me$_3$—2-Pyrazinyl | CH$_3$ | CH$_3$ | 1725 |
| 14 | 3,5,6-Me$_3$—2-Pyrazinyl | CH$_3$ | CH$_3$ | |
| 15 | 3,5,6-Me$_3$—2-Pyrazinyl | Me$_2$CH— | H | 1720 |
| 16 | 3,5,6-Me$_3$—2-Pyrazinyl | CH$_3$ | CH$_3$ | |
| 17 | 3-Me—2-Pyrazinyl | CH$_3$ | CH$_3$ | 1720 |
| 18 | 3,5,6-Me$_3$—2-Pyrazinyl | —(CH$_2$)$_4$— | | 1720 |
| 19 | 2-Pyridinyl | H | H | 1710 |
| 20 | 2-Pyridinyl | n-C$_6$H$_{12}$— | H | 1730 |
| 21 | 6-Me—2-Pyridinyl | CH$_3$ | CH$_3$ | K.D.A.T.[a] 165°–198° C./0.3–0.4 mm. |
| 22 | (Potassium salt of Compound 21) | | | |
| 23 | 6-Me—2-pyridinyl | CH$_3$ | CH$_3$ | |
| 24 | 5-Et—2-Pyridinyl | CH$_3$ | CH$_3$ | 1725 |
| 25 | 5-Et—2-Pyridinyl | CH$_3$ | CH$_3$ | |
| 26 | 5-Et—2-Pyridinyl | CH$_3$ | CH$_3$ | |
| 27 | 6-Cl—2-Pyridinyl | CH$_3$ | CH$_3$ | CH$_3$ groups (0.7–1.4 ppm), CH$_2$ groups (2.1–2.7 ppm) aromatic H (6.6–7.7 ppm)[b] |
| 28 | 5-Me—2-Pyridinyl | Me$_2$CH— | H | 1710 |
| 29 | 2-Pyrazinyl | CH$_3$ | CH$_3$ | 1722 |
| 30 | 2-Pyrazinyl | CH$_3$ | CH$_3$ | 1722 |
| 31 | 2-Pyrazinyl | CH$_3$ | CH$_3$ | 1722 |
| 32 | 5-Me—2-Pyrazinyl | CH$_3$ | CH$_3$ | 1725 |
| 33 | 6-Me—2-Pyrazinyl | CH$_3$ | CH$_3$ | K.D.A.T.[a] 135°–173° C./0.05 mm |
| 34 | 4-Pyrimidinyl | CH$_3$ | CH$_3$ | K.D.A.T.[a] 130°–150° C./0.1–0.2 mm. |
| 35 | 6-Me—4-Pyrimidinyl | CH$_3$ | CH$_3$ | 1735 |
| 36 | 6-Me—2-Pyridinyl | CH$_3$ | CH$_3$ | |

COMPOUND

| 37 | (structure: 2-pyridinyl-CH$_2$-C(=O)-CH(CH$_3$)-CH$_2$-C(=O)-OC$_2$H$_5$) | 1710 |
| 38 | (structure: 2-pyridinyl-CH$_2$-C(=O)-CH-CH-C(=O)-OC$_2$H$_5$ with cyclohexane ring) | 1715 |
| 39 | (structure: pyridazinyl-CH$_2$-C(=O)-CH$_2$-C(CH$_3$)$_2$-CH$_2$-C(=O)-OC$_2$H$_5$) | K.D.A.T.[a] 110°–190° C./0.2–0.4 mm. |

[a]Kugelrohr distillation air temperature.
[b]$^1$H NMR spectrum in CDCl$_3$ with TMS as internal standard.

TABLE II
PYRIDINYL 1,3-DIONES

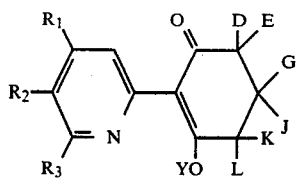

| COMPOUND | R₁ | R₂ | R₃ | D | E | G | J | K | L | Y |
|---|---|---|---|---|---|---|---|---|---|---|
| 1 | H | H | H | H | H | CH₃ | CH₃ | H | H | H |
| 2 | H | H | H | H | H | CH₃ | CH₃ | H | H | Na |
| 3 | CH₃ | H | H | H | H | CH₃ | CH₃ | H | H | H |
| 4 | H | H | H | H | H | CH(CH₃)₂ | H | H | H | H |
| 5 | CH₃ | H | H | H | H | CH(CH₃)₂ | H | H | H | H |
| 6 | C₂H₅ | H | H | H | H | CH(CH₃)₂ | H | H | H | H |
| 7 | CH₃O | H | H | H | H | CH(CH₃)₂ | H | H | H | H |
| 8 | H | H | H | H | H | —(CH₂)₄— | | H | H | H |
| 9 | H | H | H | H | H | C₂H₅ | CH₃ | H | H | H |
| 10 | H | H | H | H | H | CH(CH₃)(C₂H₅) | H | H | H | H |
| 11 | H | H | H | H | H | C(CH₃)₃ | H | H | H | H |
| 12 | H | H | H | H | H | CH(C₂H₅)₂ | H | H | H | H |
| 19 | H | H | H | H | H | H | H | H | H | H:HCl |
| 20 | H | H | H | H | H | C₆H₁₂ | H | H | H | H |
| 21 | H | H | CH₃ | H | H | CH₃ | CH₃ | H | H | H |
| 22 | H | H | CH₃ | H | H | CH₃ | CH₃ | H | H | K |
| 23 | H | H | CH₃ | H | H | CH₃ | CH₃ | H | H | COCH(CH₃)₂ |
| 24 | H | C₂H₅ | H | H | H | CH₃ | CH₃ | H | H | H |
| 25 | H | C₂H₅ | H | H | H | CH₃ | CH₃ | H | H | COCH₃ |
| 26 | H | C₂H₅ | H | ·H | H | CH₃ | CH₃ | H | H | COC₅H₁₁ |
| 27 | H | H | Cl | H | H | CH₃ | CH₃ | H | H | H |
| 28 | H | CH₃ | H | H | H | CH(CH₃)₂ | H | H | H | H |
| 36 | H | H | CH₃ | H | H | CH₃ | CH₃ | H | H | COC₇H₁₅ |

37 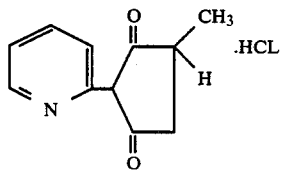

38 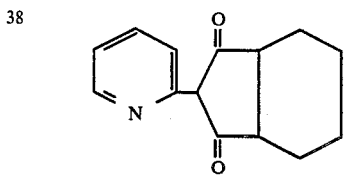

TABLE II
PYRAZINYL 1,3-DIONES

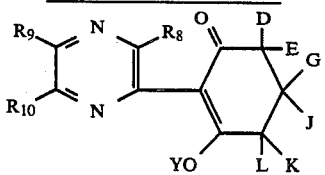

| COMPOUND | R₈ | R₉ | R₁₀ | D | E | G | J | K | H | Y |
|---|---|---|---|---|---|---|---|---|---|---|
| 13 | CH₃ | CH₃ | CH₃ | H | H | CH₃ | CH₃ | H | H | H |
| 14 | CH₃ | CH₃ | CH₃ | H | H | CH₃ | CH₃ | H | H | COC₅H₁₁ |
| 15 | CH₃ | CH₃ | CH₃ | H | H | (CH₃)₂CH | H | H | H | H |
| 16 | CH₃ | CH₃ | CH₃ | H | H | (CH₃)₂CH | H | H | H | COC₅H₁₁ |
| 17 | CH₃ | H | H | H | H | CH₃ | CH₃ | H | H | COCH(CH₃)₂ |
| 18 | CH₃ | CH₃ | CH₃ | H | H | —(CH₂)₄— | | H | H | H |

TABLE II-continued
PYRAZINYL 1,3-DIONES

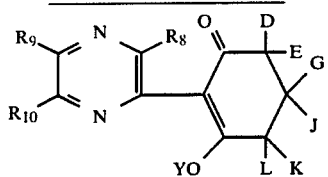

| COMPOUND | $R_8$ | $R_9$ | $R_{10}$ | D | E | G | J | K | H | Y |
|---|---|---|---|---|---|---|---|---|---|---|
| 29 | H | H | H | H | H | $CH_3$ | $CH_3$ | H | H | H |
| 30 | H | H | H | H | H | $CH_3$ | $CH_3$ | H | H | $COCH(CH_3)_2$ |
| 31 | H | H | H | H | H | $CH_3$ | $CH_3$ | H | H | $COC_7H_{15}$ |
| 32 | H | $CH_3$ | H | H | H | $CH_3$ | $CH_3$ | H | H | H |
| 33 | H | H | $CH_3$ | H | H | $CH_3$ | $CH_3$ | H | H | H |

TABLE IV

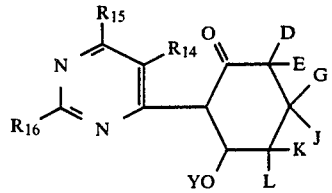

| COMPOUND | $R_{14}$ | $R_{15}$ | $R_{16}$ | D | E | G | J | K | L | Y |
|---|---|---|---|---|---|---|---|---|---|---|
| 34 | H | H | H | H | H | $CH_3$ | $CH_3$ | H | H | H |
| 35 | H | $CH_3$ | H | H | H | $CH_3$ | $CH_3$ | H | H | H |

TABLE IV-continued

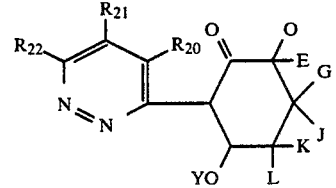

| COMPOUND | $R_{20}$ | $R_{21}$ | $R_{22}$ | D | E | G | J | K | L | Y |
|---|---|---|---|---|---|---|---|---|---|---|
| 39 | H | H | H | H | H | $CH_3$ | $CH_3$ | H | H | H |

TABLE V
PHYSICAL PROPERTIES AND ELEMENTAL ANALYSES OF HETEROCYCLIC-SUBSTITUTED 1,3-DIONES

| COMPOUND | Mp °C. | Molec. Form. | Calc'd. C | Calc'd. H | Calc'd. N | Found C | Found H | Found N |
|---|---|---|---|---|---|---|---|---|
| 1 | 163–65.5 | $C_{13}H_{15}NO_2$ | 71.86 | 6.96 | 6.45 | 71.71 | 7.00 | 6.64 |
| 3 | 122–23.5 | $C_{14}H_{17}NO_2$ | 72.70 | 7.41 | 6.06 | 72.32 | 7.47 | 6.04 |
| 4 | 110–112 | $C_{14}H_{17}NO_2$ | 72.70 | 7.41 | 6.06 | 72.59 | 7.57 | 5.92 |
| 5 | 104.5–6.5 | $C_{15}H_{19}NO_2$ | 73.44 | 7.81 | 5.71 | 73.34 | 7.79 | 5.62 |
| 6 | 74.5–77.5 | $C_{16}H_{21}NO_2$ | 74.10 | 8.16 | 5.40 | 73.98 | 8.24 | 5.39 |
| 7 | 152–54.5 | $C_{15}H_{19}NO_3$ | 68.94 | 7.33 | 5.36 | 69.30 | 7.43 | 5.41 |
| 8 | 170–71.5 | $C_{15}H_{17}NO_2$ | 74.05 | 7.04 | 5.76 | 73.75 | 6.98 | 5.76 |
| 9 | 121–22.5 | $C_{14}H_{17}NO_2$ | 72.70 | 7.41 | 6.06 | 72.85 | 7.49 | 6.11 |
| 10 | 69–72 | $C_{15}H_{19}NO_2$ | 73.44 | 7.81 | 5.71 | 73.47 | 7.82 | 5.65 |
| 11 | 145.5–48.5 | $C_{15}H_{19}NO_2$ | 73.44 | 7.81 | 5.71 | 73.31 | 7.86 | 5.78 |
| 12 | 93.5–95 | $C_{16}H_{21}NO_2$ | 74.10 | 8.16 | 5.40 | 73.33 | 8.19 | 5.25 |
| 13 | 154–55.5 | $C_{15}H_{20}N_2O_2$ | 69.20 | 7.74 | 10.76 | 68.95 | 7.79 | 10.81 |
| 14 | Oil | $C_{21}H_{30}N_2O_3$ | 70.36 | 8.43 | 7.81 | 71.3 | 8.0 | 8.2 |
| 15 | 112–30 (dec) | $C_{16}H_{22}N_2O_2.H_2O$ | 65.73 | 8.27 | 9.58 | 65.71 | 8.15 | 9.57 |
| 16 | Oil | $C_{22}H_{32}N_2O_3$ | 70.94 | 8.66 | 7.52 | 70.48 | 8.87 | 7.27 |
| 17 | 75.5–77.5 | $C_{17}H_{22}N_2O_3$ | 67.53 | 7.33 | 9.26 | 67.84 | 7.35 | 9.35 |
| 18 | 128.5–31.5 | $C_{17}H_{22}N_2O_2$ | 71.30 | 7.74 | 9.78 | 70.85 | 7.57 | 9.75 |
| 19 | 152–72 | $C_{11}H_{12}ClNO_2$ | 58.54 | 5.36 | 6.21 | 58.45 | 5.48 | 6.16 |
| 20 | 181–82.5 | $C_{17}H_{21}NO_2$ | 75.24 | 7.80 | 5.16 | 75.25 | 7.76 | 5.21 |
| 21 | 88.5–90.5 | $C_{14}H_{17}NO_2$ | 72.70 | 7.41 | 6.06 | 72.74 | 7.57 | 6.14 |
| 23 | Oil | $C_{18}H_{23}NO_3$ | 71.73 | 7.69 | 4.65 | 70.64 | 7.89 | 4.56 |
| 24 | 154.5–6.5 | $C_{15}H_{19}NO_2$ | 73.44 | 7.81 | 5.71 | 73.52 | 7.72 | 5.78 |
| 25 | Oil | $C_{17}H_{21}NO_3$ | 71.06 | 7.37 | 4.87 | 70.92 | 7.90 | 5.12 |
| 26 | Oil | $C_{21}H_{29}NO_3$ | 73.44 | 8.51 | 4.08 | 72.92 | 8.63 | 4.09 |
| 27 | 76–78 | $C_{13}H_{14}ClNO_2$ | 62.03 | 5.61 | 5.56 | 61.97 | 5.55 | 5.65 |
| 28 | 133.5–34.5 | $C_{15}H_{19}NO_2$ | 73.44 | 7.81 | 5.71 | 73.11 | 7.96 | 5.69 |
| 29 | 125.5–7.5 | $C_{12}H_{14}N_2O_2$ | 66.04 | 6.46 | 12.83 | 65.93 | 6.59 | 12.78 |
| 30 | 49.5–51.5 | $C_{16}H_{20}N_2O_3$ | 66.65 | 6.99 | 9.71 | 66.61 | 7.02 | 9.63 |
| 31 | Oil | $C_{20}H_{28}N_2O_3$ | 69.74 | 8.19 | 8.13 | 69.71 | 8.33 | 7.64 |
| 32 | 125–27.5 | $C_{13}H_{16}N_2O_2$ | 67.22 | 6.94 | 12.06 | 67.25 | 6.94 | 11.96 |
| 33 | 111–12.5 | $C_{13}H_{16}N_2O_2$ | 67.22 | 6.94 | 12.06 | 67.36 | 6.95 | 11.89 |
| 34 | 176–78 | $C_{12}H_{14}N_2O_2$ | 66.04 | 6.46 | 12.84 | 65.91 | 6.47 | 12.91 |
| 35 | 143.5–5.5 | $C_{13}H_{16}N_2O_2$ | 67.22 | 6.94 | 12.06 | 67.18 | 6.90 | 12.13 |
| 36 | Oil | $C_{22}H_{31}NO_3$ | 73.92 | 8.74 | 3.92 | 70.44 | 9.12 | 3.51 |
| 37 | 200–205 | $C_{11}H_{12}ClNO_2$ | 58.44 | 5.36 | 6.21 | 57.33 | 5.27 | 6.10 |

TABLE V-continued
PHYSICAL PROPERTIES AND ELEMENTAL ANALYSES OF HETEROCYCLIC-SUBSTITUTED 1,3-DIONES

| COMPOUND | Mp °C. | Molec. Form. | Calc'd. C | H | N | Found C | H | N |
|---|---|---|---|---|---|---|---|---|
| 38 (pyridyl-dimethyl-cyclohexanedione .HCl) | | | | | | | | |
| 39 (pyridyl-hexahydroindanedione) | 212.5-15 | C$_{14}$H$_{15}$NO$_2$ | 73.34 | 6.59 | 6.10 | 73.55 | 6.50 | 6.05 |
| (pyridazinyl-dimethyl-cyclohexanedione) | 148.5-50.5 | C$_{12}$H$_{14}$N$_2$O$_2$ | 66.04 | 6.46 | 12.84 | 65.62 | 6.39 | 12.81 |
| | 148.5-50.5 | C$_{12}$H$_{14}$N$_2$O$_2$ | 66.04 | 6.46 | 12.84 | 65.62 | 6.39 | 12.81 |

Selected heteroaryl-substituted 1,3-cycloalkanedione compounds and derivatives representative of those useful in accordance with this invention were tested with respect to their miticidal, mite ovicidal and pre-emergent and post-emergent herbicidal activity.

Suspensions of the test compounds were prepared by dissolving one gram of compound in 50 milliliters of acetone in which had been dissolved 0.1 gram (10 percent of the weight of compound) of an alkylphenoxyethanol surfactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described hereinbelow were obtained by diluting the stock suspension with water. The test procedures were as follows:

Mite Foliage Spray Test

Adults and nymphal stages of the two-spotted mite (*Tetranychus urticae* (Koch)), reared on Tendergreen bean plants at 80±5° F. and 50±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100-110 milliliters of test compound formulation by use of a DeVilbis spray gun set at 40 psig. air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5° F. and 50±5 percent relative humidity for four days, after which, a mortality count of motile forms was made on the leaves of the test plants. Any individual which was capable of locomotion upon prodding was considered living.

Mite Ovicide Test

The test organism was the egg of the two-spotted mite (*Tetranychus urticae* (Koch), as obtained from adults reared on Tendergreen bean plants under controlled conditions of 80±5° F. and 50±5 percent relative humidity. Heavily infested leaves from a stock culture were placed on the primary leaves of two bean plants six to eight inches in height, growing in a two-and-a-half inch clay pot. Females were allowed to oviposit for a period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing varying amounts of test compound per million parts of final formulation. The potted plants (one pot per compound) were placed on a revolving turntable and sprayed with 100-110 milliliters of test compound formulation by use of a DeVilbis spray gun set at 40 psig. air pressure. This application which lasted 30 seconds, was sufficient to wet the plants to run-off. As a control, 100-110 milliliters of a water solution containing acetone and emulsifier in the same concentrations as the test compound formulation, but containing no test compound, were also sprayed on plants infested with eggs. The sprayed plants were held at 80±5° F. and 50±5 percent relative humidity for four days, after which a microscopic examination was made of unhatched (dead) and hatched (living) eggs.

The results obtained are set forth in Table VI below:

TABLE VI

MITICIDAL ACTIVITY[c] OF 2-(2-PYRAZINYL)1,3-DIONES

| COMPOUND | STRUCTURE | ACTIVITY ON MITE ADULT | MITE EGG |
|---|---|---|---|
| 13 | 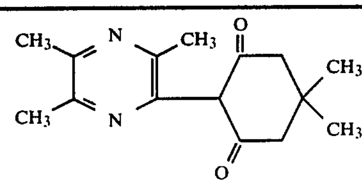 | (40) | (500) |
| 14 | 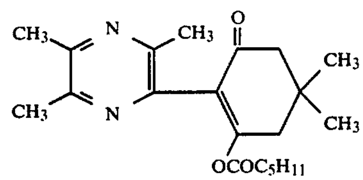 | (7) | (500) |
| 15 | 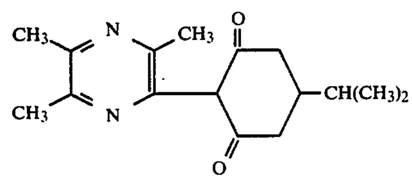 | (10) | (500) |
| 16 | 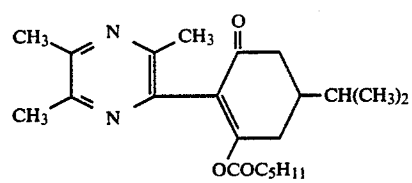 | (70) | (92) |
| 17 | 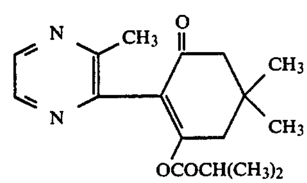 | (500) | (320) |
| 18 | 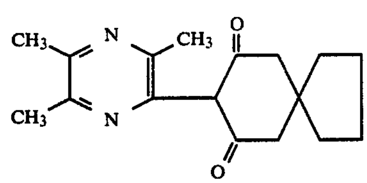 | (3) | (270) |
| 29 | 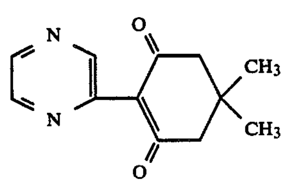 | i | i |
| 30 | 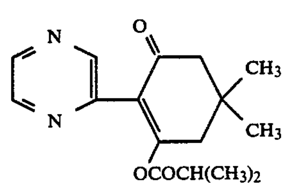 | i | i |

TABLE VI-continued

MITICIDAL ACTIVITY[c] OF 2-(2-PYRAZINYL)1,3-DIONES

| COMPOUND | STRUCTURE | ACTIVITY ON | |
|---|---|---|---|
| | | MITE ADULT | MITE EGG |
| 31 | 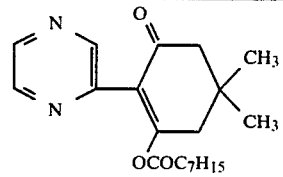 | i | i |
| 32 | 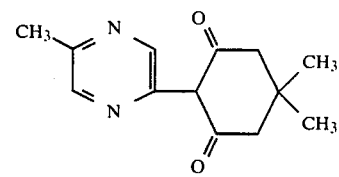 | i | i |
| 33 | 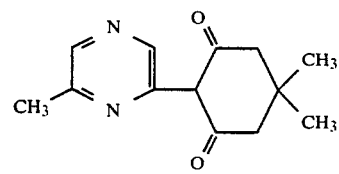 | i | i |

[c] i = inactive. Numbers in parentheses are $LD_{50}$ values. The latter refers to that concentration of test solution resulting in 50% kill when sprayed to drip-off on plant leaves.

The compounds of this invention possess activity both as pre-emergence and post-emergence herbicides and, accordingly, one aspect of this invention comprises the application of the operative materials to undesired vegetation by any means whereby said materials are brought into contact with living plants (which include seeds and germinating seedlings), e.g., by application to the soil before any plants emerge or by direct application to foliage.

The compounds are effective for both grassy weeds such as crabgrass, wild oats, barnyard grass, yellow foxtail, green foxtail, quackgrass, and rye grass, and broadleaf weeds such as mustard, pigweed, lambsquarters, and sheep sorrel are readily controlled while a broad spectrum of crops is unaffected.

The new toxicants may be applied conveniently in the form of a spray containing the active ingredient in a concentration within the range of 0.01–20.0% by weight, and preferably from 1 to 10.0% by weight. Thorough coverage of the foliage is effected for contact killing. For pre-emergence control of plants amounts within the range of 1/16 to 100 pounds per acre are generally used.

The compounds may be dispersed directly in water or a solution in an organic solvent, such as acetone, dimethylformamide, and dimethylsulfoxide emulsified in aqueous medium by the aid of a dispersing agent. As dispersing and wetting agents there may be employed soft or hard sodium or potassium soaps, alkylated aromatic sodium sulfonates such as sodium dodecylbenzenesulfonate, an amine salt as for example dibutylammonium dodecylbenzenesulfonate, alkali metal salts of sulfated fatty alcohols, ethylene oxide condensation products of alkyl phenols, or tall oil or higher mercaptans and other dispersing and wetting agents. Formulation of dry compositions is accomplished by mixing with finely divided solid carriers. Suitable carriers comprise talc, clay, pyrophyllite, silica and fuller's earth. Usually the toxicant will be only a minor proportion. The dry formulation may be used as a dust or dispersed in aqueous medium before application. If the latter it is convenient to incorporate a wetting or dispersing aid into the formulation.

Both the solid and the liquid formulations above described are useful in the application of herbicides because they facilitate uniform distribution and aid in the destruction of undesirable plants by maintaining the active ingredient in a form which enables prompt assimilation by the plant and efficient utilization of its weed destroying properties. The described conditioning agents enable the proper use by an unskilled operator without elaborate equipment to achieve the desired herbicidal effects.

The effectiveness of compounds representative of this invention as terrestrial herbicides were evaluated as pre-emergence herbicides and post-emergence herbicides. The test plants were mustard, teaweed, crabgrass and giant foxtail. For the pre-emergence test, seeds of the type of plants as shown in Table VII were sown in fresh soil. In the pre-emergence test, the soil was sprayed with a solution of the test compound immediately after the seeds were planted. The solution was about a 1% by weight solution of the test compound in acetone. The compounds were applied at the rate of 8 lbs/acre of soil surface, except where otherwise indicated in Table VII.

Approximately three weeks after spray applications, the herbicidal activity of the compound was determined by visual observation of the treated areas in comparison with untreated controls. These observations are reported in Table VII as percent control of plant growth.

In the post-emergence test the soil and developing plants were sprayed about two weeks after the seeds were sown. Except where indicated otherwise in Table VII, the compounds were applied at the rate of 8 lbs/acre from about a 1% by weight solution of the test compound in acetone. The post-emergence herbicidal activity was measured in the same way as the pre-emergence activity at three weeks following treatment.

The results are indicated in Table VII below:

TABLE VII

HERBICIDAL ACTIVITY[d]

% Control of Test Plant Indicated

| Compound | Mustard Post | Mustard Pre | Teaweed Post | Teaweed Pre | Crabgrass Post | Crabgrass Pre | Giant Foxtail Post | Giant Foxtail Pre |
|---|---|---|---|---|---|---|---|---|
| 1 | 100 | 100 | 40 | 100 | 75 | 100 | 75 | 100 |
| 2 | 100 | 100 | 100 | 80 | 100 | 100 | 100 | 100 |
| 3 | 100 | 100 | 100 | 100 | 100 | 100 | 100 | 100 |
| 4 | 100 | 100 | 100 | 100 | 100 | 90 | 100 | 100 |
| 5 | 100 | 100 | 65 | 50 | 100 | 100 | 100 | 100 |
| 6 | 100 | 0 | 100 | 50 | 100 | 30 | 100 | 70 |
| 7 | 100 | 100 | 100 | 100 | 100 | 100 | 100 | 100 |
| 8 | 100 | 95 | 100 | 100 | 100 | 80 | 100 | 80 |
| 9 | 100 | 100 | 100 | 100 | 100 | 50 | 45 | 90 |
| 10 | 100 | 100 | 100 | 100 | 100 | 60 | 100 | 80 |
| 11 | 100 | 100 | 100 | 100 | 100 | 60 | 100 | 80 |
| 12 | 100 | 80 | 30 | 0 | 0 | 0 | 30 | 0 |
| 13 | 0 | 85 | 30 | 60 | 100 | 100 | 95 | 100 |
| 14 | — | 0 | 0 | 0 | 100 | 80 | 100 | 100 |
| 15 | 40 | 40 | 70 | 30 | 100 | 100 | 100 | 100 |
| 16 | 70 | 0 | 20 | 20 | 100 | 100 | 100 | 100 |
| 17 | 90 | 30 | 20 | 20 | 100 | 90 | 100 | 100 |
| 18 | 0 | 0 | 0 | 0 | 100 | 100 | 100 | 100 |
| 19 | 100 | 80 | 100 | 20 | 55 | 20 | 50 | 0 |
| 20 | 0 | 0 | 0 | 50 | 0 | 40 | 0 | 0 |
| 21 | 99 | 100 | 80 | 100 | 45 | 50 | 20 | 50 |
| 22 | 85 | 90 | 60 | 40 | 80 | 70 | 30 | — |
| 23 | 100 | 100 | 100 | 90 | 80 | 50 | 60 | — |
| 24 | 0 | 0 | 0 | 0 | 0 | 0 | 0 | 50 |
| 25 | 0 | 0 | 50 | 0 | 50 | 0 | 0 | 0 |
| 26 | 50 | 0 | 30 | 0 | 30 | 0 | 0 | — |
| 27 | 0 | 0 | 0 | 0 | 70 | 0 | 0 | 0 |
| 28 | 50 | 0 | — | 100 | 0 | 0 | 0 | 0 |
| 29 | 55 | 0 | 60 | 0 | 80 | 0 | 80 | — |
| 30 | 40 | 30 | 30 | 0 | 100 | 0 | 100 | 0 |
| 31 | 100 | 0 | 100 | 0 | 100 | 0 | 100 | 0 |
| 32 | 60 | 0 | 20 | 40 | 100 | 80 | 100 | — |
| 33 | 60 | 0 | 0 | 0 | 80 | 0 | 30 | 0 |
| 34[e] | 0 | 50 | 0 | 60 | 0 | 0 | 0 | 0 |
| 35 | 100 | 80 | 50 | 30 | 80 | 0 | 30 | 0 |
| 36 | 100 | 95 | 0 | 20 | 95 | 60 | 0 | 50 |
| 37[f] | 30 | 0 | 30 | 0 | 0 | 0 | 0 | 0 |
| 38 | 90 | 0 | 80 | 50 | 100 | 40 | 40 | 50 |
| 39 | 50 | 0 | 0 | 0 | 40 | 0 | 0 | 0 |
| Known Compounds | | | | | | | | |
| (2-pyridyl indandione) | 40 | 0 | 0 | 0 | 60 | 50 | 0 | 0 |
| (quinolinyl dimedone) | — | 0 | 0 | 0 | 0 | 0 | 0 | 0 |
| (methylquinolinyl dimedone) | 0 | 0 | 0 | 0 | 0 | 0 | 0 | 0 |

TABLE VII-continued

HERBICIDAL ACTIVITY[d]
% Control of Test Plant Indicated

| | Mustard | | Teaweed | | Crabgrass | | Giant Foxtail | |
|---|---|---|---|---|---|---|---|---|
| | Post | Pre | Post | Pre | Post | Pre | Post | Pre |
| | 0 | 0 | 0 | 0 | 0 | 0 | 0 | 0 |

[d]Rate of application = 8 lbs. per acre.
[e]Activity on yellow nutsedge: Preemergence control = 100%.
[f]Activity on morningglory: Postemergence contol = 100%

It will be understood that the plant species employed in the above tests are merely representative of a wide variety of plants that can be controlled by the use of the compounds of this invention. The compounds contemplated in this invention may be applied as mite ovicides, miticides, and herbicides according to methods known to those skilled in the art. Compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to above 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristic for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. When used as miticides they will normally be applied to the foliage of the plants to be treated. It will be appreciated that the compounds of this invention can also be used in combination with other biologically active compounds.

Although the invention has been illustrated by the preceding examples it is not to be construed as being limited to the materials employed therein, but rather, the invention is directed to the generic area as hereinbefore disclosed. Various modifications and embodiments thereof can be made without departing from the spirit and scope thereof.

What is claimed is:

1. A compound of the formula:

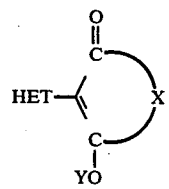

wherein
X is a 2 or 3 member alkylene chain;
Y is hydrogen, a salt forming cation, selected from Na+, NH$_4$+ and Ca++, or

wherein Z is alkyl containing up to 7 carbon atoms; and
HET is

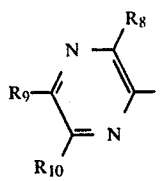

wherein $R_8$, $R_9$, and $R_{10}$ are independently hydrogen, $C_1$–$C_3$ alkyl, or $C_1$–$C_3$ alkoxy.

2. A compound according to claim 1 wherein $R_8$, $R_9$, and $R_{10}$ are alkyl and X is a 3 member alkylene chain.

3. A compound according to claim 1 wherein $R_8$, $R_9$ and $R_{10}$ are alkyl, X is a 3 member alkylene chain and Y is

4. 5,5-Dimethyl-2-(3,5,6-trimethyl-2-pyrazinyl)-1,3-cyclohexanedione.

5. 5,5-Dimethyl-3-hexanoyloxy-2-(3,5,6-trimethyl-2-pyrazinyl)-2-cyclohexene-1-one.

6. 5-(1-Methylethyl)-2-(3,5,6-trimethyl-2-pyrazinyl)-1,3-cyclohexanedione.

7. 3-Hexanoyloxy-5-(1-methylethyl)-2-(3,5,6-trimethyl-2-pyrazinyl)-2-cyclohexen-1-one.

8. 5,5-Dimethyl-3-(2-methylpropanoyloxy)-2-(3-methyl-2-pyrazinyl)-2-cyclohexene-1-one.

9. A herbicidal composition comprising an acceptable carrier and as the active toxicant a herbicidally effective amount of the compound of claim 1.

10. A method of controlling undesired plant growth which comprises subjecting said plant to a herbicidally effective amount of the compound of claim 1.

* * * * *